US011761921B2

(12) United States Patent
Xu

(10) Patent No.: US 11,761,921 B2
(45) Date of Patent: Sep. 19, 2023

(54) OUTER MEMBRANE COMPOSITIONS FOR CREATININE/CREATINE SENSORS

(71) Applicant: Instrumentation Laboratory Company, Bedford, MA (US)

(72) Inventor: Xiaoxian Xu, Maynard, MA (US)

(73) Assignee: INSTRUMENTATION LABORATORY COMPANY, Bedford, MA (US)

(*) Notice: Subject to any disclaimer, the term of this patent is extended or adjusted under 35 U.S.C. 154(b) by 700 days.

(21) Appl. No.: 16/430,057

(22) Filed: Jun. 3, 2019

(65) Prior Publication Data
US 2020/0319136 A1 Oct. 8, 2020

Related U.S. Application Data

(60) Provisional application No. 62/830,191, filed on Apr. 5, 2019.

(51) Int. Cl.
*G01N 27/327* (2006.01)
*C12Q 1/00* (2006.01)
(Continued)

(52) U.S. Cl.
CPC ......... *G01N 27/3275* (2013.01); *C12Q 1/002* (2013.01); *C12Q 1/003* (2013.01); *C12Q 1/005* (2013.01); *C12Q 1/54* (2013.01); *G01N 27/308* (2013.01); *G01N 27/3272* (2013.01); *G01N 27/3276* (2013.01); *G01N 27/3335* (2013.01); *G01N 33/5308* (2013.01); *G01N 33/70* (2013.01); *G01N 33/96* (2013.01); *G06F 17/18* (2013.01); *G16B 25/30* (2019.02);
(Continued)

(58) Field of Classification Search
CPC ............ G01N 27/3275; G01N 27/308; G01N 27/3272; G01N 27/3276; G01N 27/3335; G01N 27/3274; G01N 33/5308; G01N 33/70; G01N 33/96; G01N 33/5438; G16H 10/40; G16B 25/30; C12Q 1/002; C12Q 1/003; C12Q 1/005; C12Q 1/54; C12Q 1/58; G06F 17/18; G06G 30/331
See application file for complete search history.

(56) References Cited

U.S. PATENT DOCUMENTS 6,960,466 B2  11/2005  Pamidi et al.
7,632,672 B2  12/2009  Pamidi et al.
(Continued)

FOREIGN PATENT DOCUMENTS

EP    1753872 B1    1/2014
JP    2004528579 A    9/2004
(Continued)

OTHER PUBLICATIONS

Shin, Jae Ho, et al. "A planar amperometric creatinine biosensor employing an insoluble oxidizing agent for removing redox-active interferences." Analytical chemistry 73.24 (2001): 5965-5971. (Year: 2001).*
(Continued)

*Primary Examiner* — Robert J Eom
(74) *Attorney, Agent, or Firm* — Burns & Levinson LLP

(57) ABSTRACT

Disclosed herein are compositions for permeable outer diffusion control membranes for creatinine and creatine sensors and methods of making such membranes.

29 Claims, 3 Drawing Sheets

(51) Int. Cl.

| | | |
|---|---|---|
| G01N 27/333 | (2006.01) | |
| G01N 33/70 | (2006.01) | |
| G01N 33/96 | (2006.01) | |
| G01N 27/30 | (2006.01) | |
| C12Q 1/54 | (2006.01) | |
| G01N 33/53 | (2006.01) | |
| G16H 10/40 | (2018.01) | |
| G16B 25/30 | (2019.01) | |
| G06F 17/18 | (2006.01) | |
| C12Q 1/58 | (2006.01) | |
| G01N 33/543 | (2006.01) | |
| G06F 30/331 | (2020.01) | |

(52) U.S. Cl.
CPC ............... *G16H 10/40* (2018.01); *C12Q 1/58* (2013.01); *G01N 27/3274* (2013.01); *G01N 33/5438* (2013.01); *G06F 30/331* (2020.01)

(56) References Cited

U.S. PATENT DOCUMENTS

| | | | |
|---|---|---|---|
| 7,815,788 | B2 | 10/2010 | Schaffar et al. |
| 8,426,192 | B2 | 4/2013 | Pamidi et al. |
| 9,487,811 | B2 | 11/2016 | Zhao et al. |
| 2004/0211666 | A1 | 10/2004 | Pamidi et al. |
| 2004/0256227 | A1 | 12/2004 | Shin et al. |
| 2006/0275857 | A1 | 12/2006 | Kjaer et al. |
| 2008/0173064 | A1 | 7/2008 | Schaffar et al. |
| 2017/0254771 | A1 | 9/2017 | Balasubramanian et al. |
| 2017/0363568 | A1 | 12/2017 | Hansen et al. |
| 2020/0319136 | A1 | 10/2020 | Xu |

FOREIGN PATENT DOCUMENTS

| | | | |
|---|---|---|---|
| JP | 2008-256725 | A | 10/2008 |
| JP | 2008541103 | A | 11/2008 |
| JP | 2008541104 | A | 11/2008 |
| JP | 2008545952 | A | 12/2008 |
| JP | 2016517514 | A | 6/2016 |
| JP | 2018535421 | A | 11/2018 |
| JP | 2019039817 | A | 3/2019 |
| WO | 98/21356 | A1 | 5/1998 |
| WO | 03/019171 | A1 | 3/2003 |
| WO | 2005/052596 | A1 | 6/2005 |
| WO | 2008/028011 | A2 | 3/2008 |
| WO | 2009/053370 | A1 | 4/2009 |
| WO | 2009/082699 | A1 | 7/2009 |
| WO | 2016/096725 | A1 | 6/2016 |
| WO | 2019046281 | A1 | 3/2019 |
| WO | 2020204976 | A1 | 10/2020 |

OTHER PUBLICATIONS

International Search Report and Written Opinion for International Application No. PCT/US2019/035152, dated Nov. 8, 2019, 12 pages.
International Search Report and Written Opinion for International Application No. PCT/US2019/035155, dated Nov. 14, 2019, 12 pages.
Examiner Requisition for Canadian Patent Application No. 3,105,013, dated Jan. 26, 2022, (3 pages).
Communication pursuant to Rules 161(1) and 162 for European Patent Application No. 19740656.4, dated Nov. 12, 2021, 3 pages.
Non-Final Office Action for Korean Patent Application No. 10-2020-7037321, dated May 30, 2022, with English Translation, (6 pages).
International Preliminary Report on Patentability dated Sep. 28, 2021, International Application No. PCT/US2019/036157 filed Jun. 3, 2019 (11 pages).
First Office Action for Chinese Patent Application No. 201980043651.X, dated Mar. 8, 2022, with English Translation, (16 pages).
Nichols, Scott P et al. "The effect of nitric oxide surface flux on the foreign body response to subcutaneous implants." Biomaterials vol. 33,27 (2012): 6305-12. doi:10.1016/j.biomaterials. 2012.05.053.
Grace E. Conway et al., Layer-by-layer design and optimization of xerogel-based amperometric first generation biosensors for uric acid, Journal of Electroanalytical Chemistry, vol. 775, 2016, pp. 135-145, ISSN 1572-6657, https://doi.org/10.1016/j.jelechem. 2016.05.038.
Anders Ø. Tjell et al., Diffusion rate of hydrogen peroxide through water-swelled polyurethane membranes, Sensing and Bio-Sensing Research, vol. 21, 2018, pp. 35-39, ISSN 2214-1804, https://doi.org/10.1016/j.sbsr. 2018.10.001.
Decision to Grant dated Jan. 17, 2022, Japanese Application No. 2020-570972 (4 pages).
Notice of Reasons for Rejection for Japanese Patent Application No. 2020-570972, dated Sep. 28, 2021, with English translation (9 pages).
Nichols et al., The effect of nitric oxide surface flux on the foreign body response to subcutaneous implants, Biomaterials, vol. 33, No. 27, May 20, 2012, pp. 6305-6312.
Conway et al., Layer-by-layer design and optimization of xerogel-based amperometric first generation biosensors for uric acid, Journal of Electroanalytical Chemistry, vol. 775, May 25, 2016, pp. 135-145.
Tjell et al., Diffusion rate of hydrogen peroxide through water-swelled polyurethane membranes, Sensing and Bio-Sensing Research, vol. 21, No. 27, Nov. 1, 2018, pp. 35-39.
Hydrourethane AdvanSource Biomaterials, Advancesource Biomaterials, Jun. 21, 2011 [retrieved on Sep. 19, 2019]. Retrieved from the Internet URL: http://www.advbiomaterials.com/pdf/HydroThane%20Factsheet.pdf.
Hydromed D Series, Advancesource Biomaterials, Apr. 16, 2010 [retrieved on Sep. 20, 2019]. Retrieved from the Internet URL: http://www.advbiomaterials.com/products/hydrophilic/HydroMed.pdf.
International Search Report and Written Opinion for International Application No. PCT/US2019/035157, dated Dec. 12, 2019, 18 pages.
International Search Report and Written Opinion for International Application No. PCT/US2019/035153, dated Nov. 26, 2019, 12 pages.
International Search Report and Written Opinion for International Application No. PCT/US2019/035156, dated Sep. 20, 2019, 12 pages.
Second Office Action for Chinese Patent Application No. 201980043651.X, dated Aug. 4, 2022, with English Translation, (11 pages).
Decision of Final Rejection for Chinese Patent Application No. 201980043651.X, dated Nov. 21, 2022, with English Translation, (11 pages).
Communication pursuant to Article 94(3) EPC for European Patent Application No. 19740656.4, dated Dec. 12, 2022, (7 pages).
Ahyeon Koh et al: "Fabrication of nitric oxide-releasing polyurethane glucose sensor membranes", Biosensors and Bioelectronics, Elsevier Science Ltd, UK, Amsterdam, NL, vol. 28, No. 1, Jun. 12, 2011 (Jun. 12, 2011), pp. 17-24, XP028340746, ISSN: 0956-5663, DOI: 10.1016/J.BIOS.2011.06.005 [retrieved on Jun. 17, 2011].
ASTM International: "Designation: D570-98 (Reapproved 2018) Standard Test Method for", Test Method for Water Absorption of Plastics, Jan. 1, 2018 (Jan. 1, 2018), pp. 1-4, XP093004782, West Conshohocken, PA DOI: 10.1520/D0570-98R18 Retrieved from the Internet: URL:https://asrecomposite.com/wp-content/uploads/2021/07/ASTM-D-570-19982018.pdf [retrieved on Dec. 5, 2022].
Hakala K. et al.: "Monitoring water uptake of polyurethanes byin situ fluorescence technique", Journal of Applied Polymer Science, vol. 82, No. 7, Jan. 1, 2001 (Jan. 1, 2001), pp. 1593-1599, XP093004665, us ISSN: 0021-8995, DOI: 10.1002/app.1998.
Notice of Allowance for Korean Patent Application No. 10-2020-7037321, dated Dec. 13, 2022, (with English translation) (5 pages).

\* cited by examiner

OUTER MEMBRANE COMPOSITIONS FOR CREATININE/CREATINE SENSORS

CROSS REFERENCE TO RELATED APPLICATIONS

This application claims priority to and benefit of U.S. Provisional application No. 62/830,191, filed Apr. 5, 2019 and is incorporated in its entirety herein for all intents and purposes.

FIELD OF THE DISCLOSURE

The disclosure relates to diffusion control membranes for electrochemical sensors used for measuring creatinine and creatine in a sample. More particularly, the disclosure relates to compositions for permeable outer diffusion control membranes for creatinine and creatine detection and methods of making such membranes.

BACKGROUND

The ability to accurately measure creatinine and creatine levels in a patient's blood is an important indicator of renal health. In particular, serum creatinine is an important indicator of renal health because it is excreted unaltered by the kidneys, and can readily be measured. For example, elevated levels of blood serum creatinine is a late marker of chronic kidney disease, and is generally only observed when significant kidney damage has already occurred.

Creatinine and creatine concentrations in a sample (e.g., a patient's blood) may be measured via electrochemical sensors. For example, current creatinine sensors may include an enzymatic biosensor containing three enzymes-creatininase, creatinase, and sarcosine oxidase—that catalyze the production of glycine, formaldehyde, and hydrogen peroxide from creatinine and water. These three enzymes may be immobilized on the surface of a platinum electrode, and the final reaction product of hydrogen peroxide ($H_2O_2$) may then be electrochemically oxidized on the platinum electrode under a constant polarization potential and used to measure creatinine/creatine in a patient's blood. Due to the presence of creatine in clinical samples, an additional sensor for creatine measurement is required for correcting the creatine response of the creatinine sensor. Such creatine sensors include an enzymatic biosensor containing two enzymes-creatinase and sarcosine oxidase.

On both creatinine and creatine sensors, there is a diffusion control membrane (also referred to as an outer membrane) on top of the enzyme layer. The diffusion control membrane limits the flux of creatinine and creatine substrates entering the enzyme layer to ensure that the signals generated by the hydrogen peroxide are proportional to the substrate concentrations of the sample.

Theoretically, the creatinine measuring system described above can quantitatively measure creatinine in biological samples, however several factors can create challenges to obtaining accurate creatinine measurements. One factor, creatine interference, is typically dealt with by using a separate creatine sensor and subtracting the creatine concentration as a correction measure. However, large errors can be introduced when creatine concentrations are high (e.g., [creatine]>>[creatinine]). Another factor, slow baseline recovery, can create errors if unreacted substrates are not removed immediately after sample measurement because unremoved substrates will continue to generate current signal. A third factor relates to biological sample matrix effect and biocompatibility. For example, when exposed to a biological sample matrix such as whole blood, some outer diffusion membranes can exhibit severe sensitivity and baseline change due to protein fouling or surface hydrophobicity changes and micro clot formation.

Currently available outer diffusion control membranes for creatinine sensors include polymeric materials such as polycarbonate, poly 2-hydroxyethyl methacrylate (polyHEMA) and polyurethane. However, such diffusion membranes do not address all three of the limitations mentioned above. Accordingly, there is an urgent unmet need to identify and develop new compositions to improve outer membrane properties to address problems due to creatine interference, slow baseline recovery and biological sample matrix effects and biocompatibility.

SUMMARY

Disclosed herein are diffusion membrane compositions, methods of making, biosensors containing such diffusion membranes and cartridges housing biosensors containing such diffusion membranes. The biosensors containing the diffusion membranes are creatinine/creatine biosensors. The terms diffusion membrane and outer membrane are used interchangeably throughout this disclosure. Also, the terms biosensor and sensor are used interchangeably throughout this disclosure.

In one aspect, diffusion membrane compositions are provided including at least two different types of polyurethane materials. The different types of polyurethane materials have different properties including different water uptake percentages and different shore hardness values. The w/w amounts of the different types of polyurethane materials are adjusted to result in diffusion membranes having a creatinine to creatine diffusion ratio of at least 2.0, preferably 2.0-2.5, more preferably 2.5-3.0 and most preferably at least 3.0. The w/w amounts of the different types of polyurethane materials are also adjusted to result in diffusion membranes having a creatinine slope of at least 1800, preferably at least 1900 and more preferably at least 2000.

In some embodiments, the polyurethane materials used in the diffusion membrane compositions have water uptake percentages that are about 3%-60%. Representative examples of polyurethane materials include 3% water uptake polyurethane, 20% water uptake polyurethane, 50% water uptake polyurethane and 60% water uptake polyurethane.

In some embodiments, the 50% water uptake polyurethane is present in the diffusion membrane compositions in an amount of greater than 0% w/w. In other embodiments, the 50% water uptake polyurethane is present in the diffusion membrane compositions in an amount up to 65% w/w. In some embodiments, the 20% water uptake polyurethane is present in the diffusion membrane compositions in an amount up to 69% w/w. In some embodiments, the 3% water uptake polyurethane is present in the diffusion membrane compositions in an amount up to 33% w/w. In some embodiments, the 60% water uptake polyurethane is present in the diffusion membrane compositions in an amount up to 67% w/w.

In some embodiments, the diffusion membrane compositions include at least two different types of polyurethane. Representative examples of diffusion membrane compositions including two different types of polyurethane include a mixture of 20% water uptake polyurethane and 60% water uptake polyurethane, a mixture of 20% water uptake polyurethane and 50% water uptake polyurethane and a mixture of 60% water uptake polyurethane and 50% water uptake polyurethane. In some embodiments, the diffusion membrane compositions include 50-55% w/w of 20% water uptake polyurethane and 45-50% w/w of 60% water uptake polyurethane. In certain embodiments, the diffusion membrane compositions include 50% w/w of 20% water uptake polyurethane and 50% w/w of 60% water uptake polyurethane. In other embodiments, the diffusion membrane compositions include 55% w/w of 20% water uptake polyurethane and 45% w/w of 60% water uptake polyurethane. In further embodiments, the diffusion membrane compositions include 50% w/w of 20% water uptake polyurethane and 50% w/w of 50% water uptake polyurethane. In yet further embodiments, the diffusion membrane compositions include 50% w/w of 60% water uptake polyurethane and 50% w/w of 50% water uptake polyurethane.

In some embodiments, the diffusion membrane compositions include at least three different types of polyurethane. For example, a diffusion membrane composition including three different types of polyurethane includes a mixture of 20% water uptake polyurethane, 50% water uptake polyurethane and 60% water uptake polyurethane. In some embodiments, the diffusion membrane compositions include 33.3% w/w of 20% water uptake polyurethane, 33.3% w/w of 60% water uptake polyurethane and 33.3% w/w of 50% water uptake polyurethane. In other embodiments, the diffusion membrane compositions include 69% w/w of 20% water uptake polyurethane, 2% w/w of 60% water uptake polyurethane and 29% w/w of 50% water uptake polyurethane.

In some embodiments, the diffusion membrane compositions include at least four different types of polyurethane. For example, a diffusion membrane composition including four different types of polyurethane includes a mixture of 3% water uptake polyurethane, 20% water uptake polyurethane, 50% water uptake polyurethane and 60% water uptake polyurethane. In some embodiments, the diffusion membrane compositions include 12.5% w/w of 20% water uptake polyurethane, 12.5% w/w of 3% water uptake polyurethane, 62.5% w/w of 60% water uptake polyurethane and 12.5% w/w of 50% water uptake polyurethane. In other embodiments, the diffusion membrane compositions include 12.5% w/w of 20% water uptake polyurethane, 12.5% w/w of 3% water uptake polyurethane, 12.5% w/w of 60% water uptake polyurethane and 62.5% w/w of 50% water uptake polyurethane. In further embodiments, the diffusion membrane compositions include 8% w/w of 20% water uptake polyurethane, 23% w/w of 3% water uptake polyurethane, 4% w/w of 60% water uptake polyurethane and 65% w/w of 50% water uptake polyurethane. In yet further embodiments, the diffusion membrane compositions include 11% w/w of 20% water uptake polyurethane, 11% w/w of 3% water uptake polyurethane, 67% w/w of 60% water uptake polyurethane and 11% w/w of 50% water uptake polyurethane.

In another aspect, a method of making the diffusion membrane compositions disclosed herein is provided. The method includes the steps of: a) dissolving at least two different polyurethane resins in an organic solvent or mixture of solvents to create a polyurethane mixture; b) casting a layer of the polyurethane mixture onto a support material; c) allowing the solvent or mixture of solvents to evaporate; and d) repeating steps b) and c) 1-3 times.

In some embodiments of the method, the polyurethane materials (e.g. resins) used in the diffusion membrane compositions have water uptake percentages that are about 3%-60% as described above for the compositions. In some embodiments of the method, the w/w amounts of the different types of polyurethane materials are adjusted to result in diffusion membranes having a creatinine to creatine diffusion ratio of at least 2.0, preferably 2.0-2.5, more preferably 2.5-3.0 and most preferably at least 3.0. The w/w amounts of the different types of polyurethane materials are also adjusted to result in diffusion membranes having a creatinine slope of at least 1800, preferably at least 1900 and more preferably at least 2000.

In some embodiments of the method, the polyurethane materials are dissolved in organic solvent(s) including methylene chloride, dimethylformamide, dimethylacetamide, tetrahydrofuran, cyclohexanone, isopropanol or mixtures thereof.

In some embodiments of the method, the support material is an electrode having an enzyme layer immobilized thereon. In certain embodiments, the electrode is made of carbon, graphite or carbon nanotubes. In other embodiments, the electrode is made of metal. Representative examples of metals of the electrodes include platinum, gold, palladium, or alloys of platinum, gold and palladium. In some embodiments of the method, the enzyme layer includes a plurality of enzymes including creatininase, creatinase, sarcosine oxidase and combinations thereof. The enzyme layer is positioned between the outer diffusion membrane and the electrode.

In some embodiments of the method, steps b) and c) are repeated two times.

In another aspect, a biosensor is provided. In some embodiments, the biosensor includes an electrode, a plurality of enzymes immobilized on the electrode forming an enzyme layer and a diffusion membrane disposed onto the surface of the enzyme layer.

In some embodiments of the biosensor, the polyurethane materials (e.g. resins) used in the diffusion membrane compositions have water uptake percentages that are about 3%-60% as described above for the compositions. In some embodiments of the biosensor, the w/w amounts of the different types of polyurethane materials are adjusted to result in diffusion membranes having a creatinine to creatine diffusion ratio of at least 2.0, preferably 2.0-2.5, more preferably 2.5-3.0 and most preferably at least 3.0. The w/w amounts of the different types of polyurethane materials are also adjusted to result in diffusion membranes having a creatinine slope of at least 1800, preferably at least 1900 and more preferably at least 2000.

In certain embodiments of the biosensor, the electrode is made of carbon, graphite or carbon nanotubes. In other embodiments, the electrode is made of metal. Representative examples of metals of the electrodes include platinum, gold, palladium, or alloys of platinum, gold and palladium. In some embodiments of the biosensor, the enzyme layer includes a plurality of enzymes including creatininase, creatinase, sarcosine oxidase and combinations thereof. The enzyme layer is positioned between the outer diffusion membrane and the electrode. The biosensor is used to measure creatine and/or creatinine in a body fluid sample such as blood, plasma or serum.

In a further aspect, a disposable cartridge housing the biosensor described herein is provided. In some embodiments of the disposable cartridge, the biosensor described herein is one sensor in a sensor array. In some embodiments of the disposable cartridge, the biosensor includes an electrode, a plurality of enzymes immobilized on the electrode forming an enzyme layer and a diffusion membrane disposed onto the surface of the enzyme layer and the diffusion membrane is adjacent to a body fluid sample flow chamber.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

DETAILED DESCRIPTION

Figure 1A:
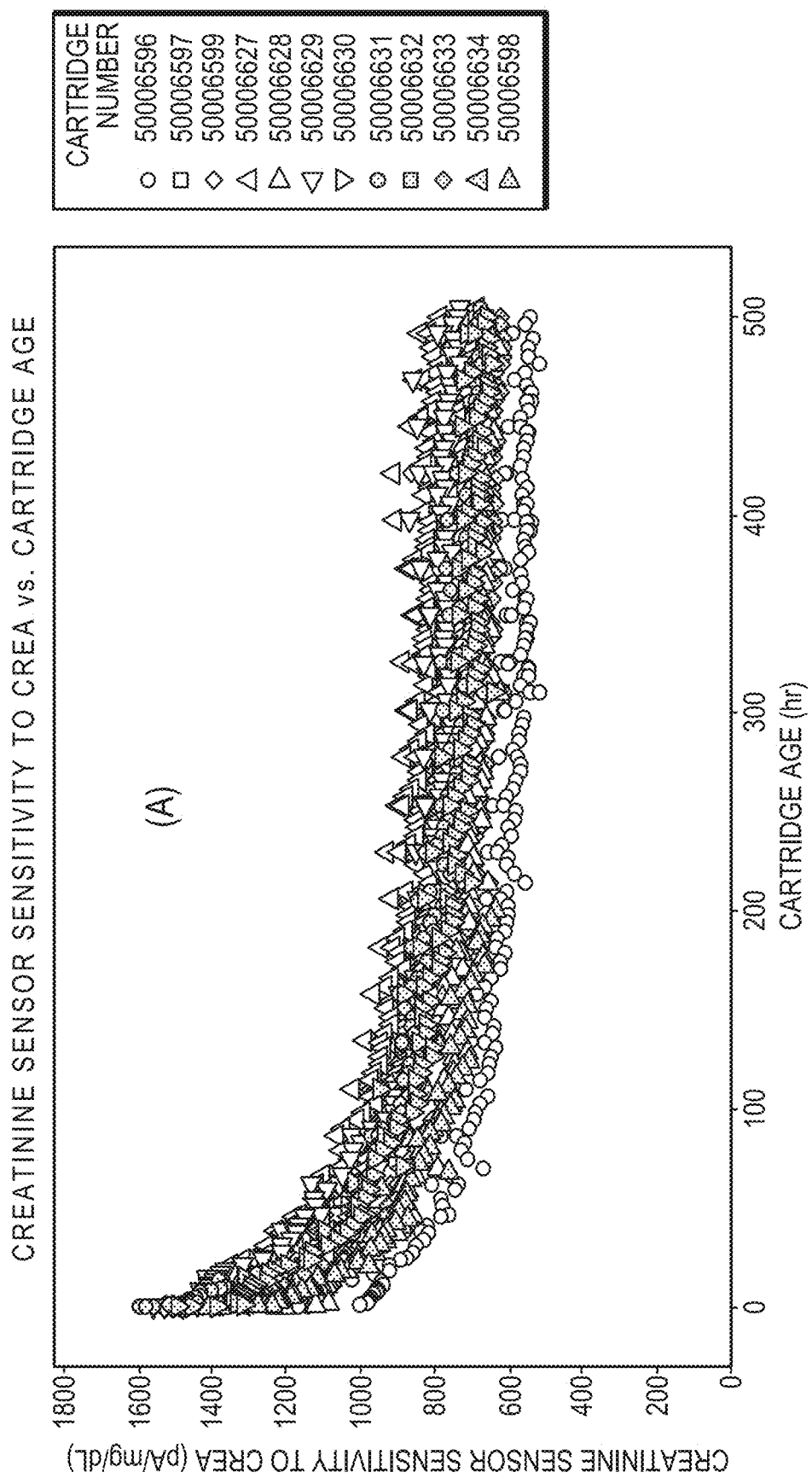
FIG. 1A is a graph of creatinine sensor sensitivity to creatinine (Crea) in a group of 12 cartridges, the sensitivity to creatinine of each cartridge plotted as slope, picoampere/milligram/deciliter (pA/mg/dL) versus age of cartridge (hours), over a three week use period after 5-month room temperature storage. Each cartridge includes an outer diffusion membrane of formula F20 (see Table 2).

The present disclosure is based, at least in part, on the discovery that diffusion control membranes (i.e. outer membranes) made from blends different types of polyurethane can limit creatine interference, allow for quick baseline recovery and limit biological sample matrix effects. The present disclosure provides diffusion membrane compositions including at least two different types of polyurethane and having a creatinine to creatine diffusion ratio of at least 2.0. The present disclosure also provides methods of making such diffusion membrane compositions and biosensors using such diffusion membranes.

Current creatinine sensors in a creatine/creatinine system (e.g., GEM PAK cartridge) include an enzymatic biosensor containing three enzymes. These enzymes are immobilized on the surface of a platinum electrode. The creatinine detection is based on three enzyme cascade reaction:

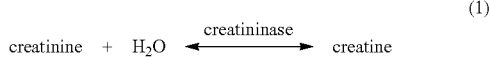
(1)

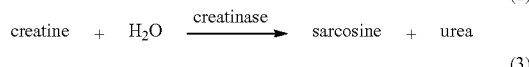
(2)

(3)

The product hydrogen peroxide ($H_2O_2$) is then electrochemically oxidized on the platinum electrode under the constant polarization potential.

The presence of creatine in clinical samples necessitates an additional sensor for creatine measurement to correct the creatine response of the creatinine sensor. The creatine sensor includes steps (2) and (3) of the above enzyme cascade reactions.

In order to determine the respective concentrations of creatinine and creatine in a biological sample(s), the creatinine and creatine sensors need to be calibrated in order to determine their respective sensitivities. This may be achieved by comparing the readings of the creatinine and creatine sensors in calibration solutions containing predetermined concentrations of creatinine and creatine. Once the sensitivities of the creatinine and creatine sensors are determined, the concentrations of creatine and creatinine in any biological sample can be estimated by adjusting the measured readings with the results determined from the calibration process.

Both the creatine and creatinine sensors also have a diffusion control membrane (also referred to as an outer membrane) on top of the enzyme layers. The diffusion control membrane limits the flux of creatinine and creatine substrates entering the enzyme layer to ensure that the signals generated by the hydrogen peroxide are proportional to the substrate concentrations of the sample.

Theoretically, a creatinine measurement system as described above may quantitatively measure the concentration of creatinine in biological samples. However, there are several practical issues associated with sensor variations that result from typical manufacturing processes, calibration and other analyzer operation specific variations, and biological sample matrix variations that present significant challenges with respect to measuring creatinine accurately including, for example, the following.

1. Creatine interference. It is known from literature that biological samples (e.g., whole blood) contain both creatinine and creatine and the Crea sensor, using the three enzyme cascade reaction of converting creatinine to hydrogen peroxide, measures the total response of both creatinine and creatine in the blood sample. Most measurement methodologies involve subtracting the response attributable to creatine as a correction by measuring the blood creatine with a separate creatine sensor including two enzymes as described above. This method assumes that all of the factors in blood samples that impact the creatine response on both creatinine and creatine sensors (e.g., $HCO_3^-$, hematocrit, blood matrix, etc.) are identical and will be cancelled out during the correction. However, large errors result when creatine concentrations are high (e.g., [Cr]>>[Crea]). The present invention solves the problem of creatine interference by suppressing the creatine signal of enzyme sensors by providing outer membrane compositions having permeabilities in favor of creatinine diffusion over creatine diffusion so that the impact from creatine interference is minimized with a differential measurement.

2. Baseline recovery. With the enzyme cascade reactions of creatinine and creatine biosensors, only portions of the substrates, creatinine and creatine, that diffuse through the outer membrane are converted to product. The remaining substrates will continuously generate current signal if not immediately removed after sample measurement. This slow change in background current causes errors in subsequent sample measurements. The present invention solves the problem of slow baseline recovery by providing outer membrane compositions having permeabilities that quickly allow the substrates to diffuse in during sample measurement and out after sample measurement is completed.

3. Biological sample matrix effect and biocompatibility. When exposed to a biological sample matrix, such as whole blood, some outer diffusion control membranes may have severe sensitivity and baseline change due to protein fouling or surface hydrophobicity changes and micro clot formation. Creatinine concentrations in biological samples are very low (0.04-1.10 mg/dL) compared to some other components of the sample matrix (e.g., glucose is present at concentrations of 65-95 mg/dL). Low concentrations of creatinine in biological samples, further reduction of creatinine amounts due to limited diffusion through outer membranes, and the three enzyme conversion process of the biosensor result in very low electrical signals. Because the electrical signals generated are very small, interference from high concentration drugs or common chemicals in biological sample matrices can dominate the creatinine sample response causing error in clinical sample measurements. The present invention solves the problem of biological sample matrix effects and biocompatibility by providing outer membrane compositions having minimal matrix effects.

The present invention disclosure describes polyurethane based outer membrane compositions for creatinine/creatine biosensors and methods of making such membranes. The membranes disclosed herein have a permeability for creatinine that is 2 to 3 times higher than the permeability for creatine. This differential in permeability provides an advantageous Crea/Cr signal ratio for such biosensors. The outer membrane compositions disclosed herein also facilitate fast removal of the substrate(s) from the enzyme layer and have a quick baseline recovery after sample exposure and wash. In addition, the outer membrane compositions disclosed herein exhibit superior biocompatibility having little or no micro-clot formation, and minimizing protein fouling and permeability changes when in contact with whole blood samples.

Polyurethane (PU) is a polymer having superior biocompatibility in many successful in vivo and in vitro applications in medical devices. Hydrophilic medical grade polyurethane families were used in the compositions of the outer membranes as disclosed herein, including Tecophlic™ and Tecoflex™ from Lubrizol (Ohio, USA) and HydroMed™ D series from AdvanSource Biomaterials (Massachusetts, USA). These commercially available polymeric resins or solutions are aliphatic, polyether-based polyurethane, which can be dissolved in organic solvents or mixtures of solvents such as methylene chloride, dimethylformamide (DMF), dimethylacetamide (DMA), tetrahydrofuran (THF), cyclohexanone, isopropanol, etc. Within these polyurethane families, there are different grades of materials available with various combinations of hardness and water uptake levels.

The permeability of a substance going through a mass transfer polymer membrane mainly depends on its molecular structure, hydrophobicity and charge. The polymer membranes disclosed herein are a mixture of more than one polymer, and the permeability of a substance through such membranes also depends on the molecular structure, hydrophobicity and charge of the polymer membrane composition.

As used herein, "creatine (a.k.a., 2-[Carbamimidoyl (methyl)amino]acetic acid, N-Carbamimidoyl-N-methyl-glycine, or Methylguanidoacetic acid)" refers to an organic compound that produce energy for the cells through the recycling of adenosine triphosphate (ATP) by converting adenosine diphosphate (ADP) back to ATP by donating phosphate groups. Creatine has the following chemical structure:

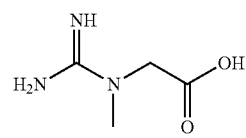

2-[Carbarmimidoyl(methyl)amino]acetic acid

As used herein, "creatinine" refers to the enzymatic breakdown by-product of creatine, and is generally found in two major tautomeric forms, which are shown below.

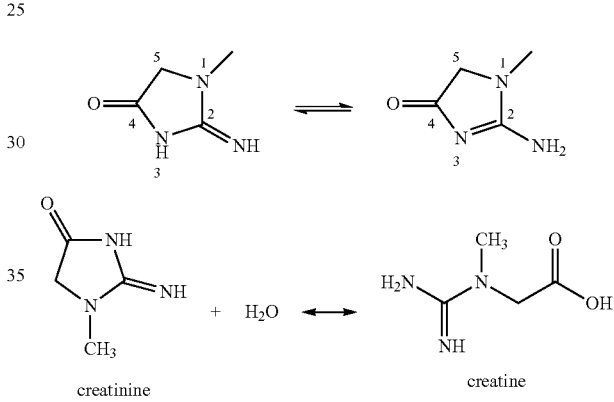

creatinine          creatine

As shown in the diagram above, the significant difference in molecular structure of creatinine (cyclic compound) versus creatine (linear compound) makes it possible to modify or regulate the diffusion rate of creatinine and creatine through a polymer membrane composition based on the polymer material properties (structure, hydrophobicity and charge), the mix ratio of multiple polymers and the casting process (solid concentrations, number of layers and solvent selection).

Outer membrane compositions that not only have the best diffusion rate for creatinine but also have a maximum Crea/Cr ratio to minimize creatine interference were developed by varying critical factors of the membrane composition: polyurethane type (hardness 20-85, water uptake: 3% to 100%), % w/v solid of casting solution (2-10%), solvent type and solvent ratio (for example, THF, cyclohexanone, and the mixture of the two with a ratio between 50-100%). It should be noted that the solvents play an important role when the membrane is formed through a solvent casting process. That is, since different solvents evaporate at different rates, the evaporation rate will impact the morphology and orientation of internal polymer chains as well as the adhesion of the membrane to a support material.

A group of formulations were obtained through experiments that meet the requirements of having high sensitivity for creatinine and a Crea/Cr ratio≥2. Subsequent screening tests were conducted to evaluate the sensor performance stability upon exposure to whole blood samples. The accuracy of reported creatinine concentration compared to a reference method and the stability of sensor sensitivity over the use life were evaluated. Some of the outer membrane formulations had initial high sensitivity but showed significant changes after exposure to whole blood samples. Without wishing to be bound by theory, some explanations for this phenomena are that the total weight % solid material was too low so pin holes may have formed in the membrane during drying or that the composition of the mixed polyurethanes was too hydrophilic and the diffusion rate changed significantly when protein and lipid in the blood coated on the surface which led to a drop in sensor sensitivity. The outer membrane composition formulations are discussed in more detail in the following examples.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1. Application of a Simplex-Centroid Mixture Design to Obtain Outer Membrane Formulations Based on 3 Commercially Available Polyurethane (PU) Families Four polyurethane materials (PU1-PU4) were selected from Tecophlic™, Tecoflex™ and HydroMed™ D families covering Shore Hardness from 20-80, and water uptake levels from 3-60%. Experiments were designed to investigate the relationship of the permeability of each component and various 2-, 3- and 4-component mixtures with creatinine and creatine slopes. Since there are other factors that may play roles in sensor slope, all of the test PU solutions were kept at a concentration of 7% w/v and a solvent ratio of 85/15 of THF/cyclohexanone. The casting conditions were also kept constant at two layers for each testing PU solution. The outer membranes were cured at room temperature for 5-10 minutes for each layer for solvent evaporation.

A simplex-centroid mixture design using four types of polyurethane (PU1-PU4) was applied to 18 design points (F1-F18) are listed in Table 1 related to the PU raw material characteristics (hardness and water uptake). The concentration ranges tested for each PU component were 0-7% w/v. Twelve sensors were prepared with each of the 18 PU formulations and the mean slope values (in units of pico-ampere per milligram/deciliter, pA/mg/dL) towards creatinine and creatine for each formulation are summarized in Table 1.

TABLE 1

PU compositions of 18 simplex-centroid mixture designs and corresponding sensor slope

| | Relative % of PU type | | | | Mean Slope and Ratio | | |
| --- | --- | --- | --- | --- | --- | --- | --- |
| Formulation ID | PU1 | PU2 | PU3 | PU4 | (pA/mg/dL) | | |
| Shore Hardness | 60 | 80 | 60 | n/a | (N = 12) | | |
| Water uptake % | 20 | 3 | 60 | 50 | Crea | Cr | Crea/Cr |
| F1 | 100.0 | 0.0 | 0.0 | 0.0 | 1025 | 237 | 4.3 |
| F2 | 0.0 | 0.0 | 100.0 | 0.0 | 2213 | 638 | 3.5 |
| F3 | 0.0 | 0.0 | 0.0 | 100.0 | 1862 | 1151 | 1.6 |
| F4 | 50.0 | 50.0 | 0.0 | 0.0 | N/A | 71 | N/A |
| F5 | 50.0 | 0.0 | 50.0 | 0.0 | 1987 | 589 | 3.4 |
| F6 | 50.0 | 0.0 | 0.0 | 50.0 | 2232 | 739 | 3.0 |
| F7 | 0.0 | 50.0 | 50.0 | 0.0 | N/A | 11 | N/A |
| F8 | 0.0 | 50.0 | 0.0 | 50.0 | 666 | 382 | 1.7 |
| F9 | 0.0 | 0.0 | 50.0 | 50.0 | 2564 | 1039 | 2.5 |
| F10 | 33.3 | 33.3 | 33.3 | 0.0 | 106 | 79 | 1.3 |
| F11 | 33.3 | 33.3 | 0.0 | 33.3 | N/A | 35 | N/A |
| F12 | 33.3 | 0.0 | 33.3 | 33.3 | 2308 | 763 | 3.0 |
| F13 | 0.0 | 33.3 | 33.3 | 33.3 | 1539 | 631 | 2.4 |
| F14 | 25.0 | 25.0 | 25.0 | 25.0 | 1108 | 435 | 2.5 |

TABLE 1-continued

PU compositions of 18 simplex-centroid mixture designs and corresponding sensor slope

| | Relative % of PU type | | | | Mean Slope and Ratio (pA/mg/dL) (N = 12) | | |
|---|---|---|---|---|---|---|---|
| Formulation ID | PU1 | PU2 | PU3 | PU4 | | | |
| Shore Hardness | 60 | 80 | 60 | n/a | | | |
| Water uptake % | 20 | 3 | 60 | 50 | Crea | Cr | Crea/Cr |
| F15 | 62.5 | 12.5 | 12.5 | 12.5 | 1080 | 300 | 3.6 |
| F16 | 12.5 | 62.5 | 12.5 | 12.5 | N/A | 9 | N/A |
| F17 | 12.5 | 12.5 | 62.5 | 12.5 | 1935 | 614 | 3.2 |
| F18 | 12.5 | 12.5 | 12.5 | 62.5 | 2410 | 1068 | 2.3 |

The results in Table 1 indicate that the creatinine permeability is directly proportional to the water uptake level of the PU material tested. PU2, with extremely low water uptake of 3%, blocks the diffusion of creatinine and creatine and will not generate useful sensor signals if an outer membrane composition contains 33% or higher of PU2.

On the other hand, in addition to water uptake, creatine diffusion is also PU-type dependent. Creatine has highest permeability with the PU4 membrane (mean slope of 1151 pA/mg/dL) versus the PU3 membrane (mean slope of 638 pA/mg/dL); the PU4 membrane having a 50% water uptake and the PU3 membrane having a 60% water uptake. This difference in permeability between creatinine and creatine provides the possibility of maximizing the Crea/Cr signal ratio while still maintaining a high creatinine signal by adjusting the PU material and composition. For example, F5 provides a similarly high creatinine slope to F3 (1987 vs. 1862 pA/mg/dL), but F5 has a Crea/Cr ratio that is two times more than that of F3 (3.4 vs. 1.6), thus providing a better sensor in terms of less creatine interference effect.

Based on the test results of the 18 PU formulations shown in Table 1, the creatinine slope is a function of the PU mixtures. Thus, a target creatinine sensor slope for creatinine and creatine can be achieved with a mixture of two to four polyurethanes. For example, with a set target of 2000 pA/mg/dL for creatinine slope, various formulations can be obtained using regression modeling (Table 2).

TABLE 2

PU outer membrane formulations obtained by regression modeling with a set target of 2000 pA/mg/dL for creatinine slope

| Formulation | Relative % of PU type | | | | Predicted Slope and Ratio (pA/mg/dL) | | |
|---|---|---|---|---|---|---|---|
| ID | PU1 | PU2 | PU3 | PU4 | Crea | Cr | Crea/Cr |
| F19 | 8% | 23% | 4% | 65% | 2007 | 973 | 2.06 |
| F20 | 55% | 0% | 45% | 0% | 2000 | 555 | 3.60 |
| F21 | 69% | 0% | 2% | 29% | 2008 | 570 | 3.52 |
| F22 | 11% | 11% | 67% | 11% | 2014 | 568 | 3.55 |

Example 2: Use of F20 in a Creatinine Sensor

Formulation F20 applied onto a creatinine sensor demonstrated stable sensitivities toward both creatinine and creatine, and had a Crea/Cr signal ratio of about 3 as shown in Table 3. Both sensor sensitivities and the Crea/Cr ratio were stable over a 5-month shelf life at ambient storage.

Figure 1B:
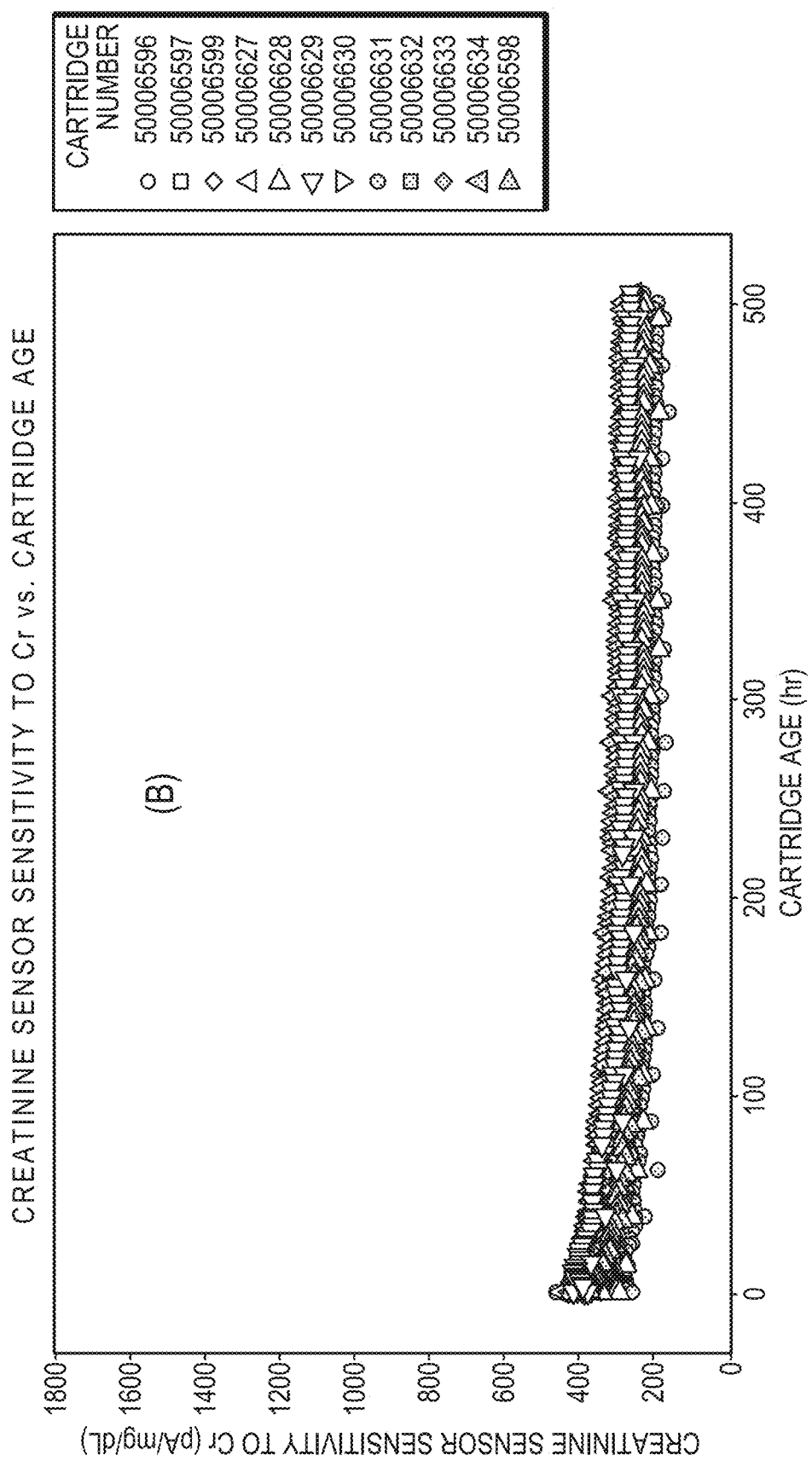
FIG. 1B is a graph of creatinine sensor sensitivity to creatine (Cr) in a group of 12 cartridges, the sensitivity to creatine of each cartridge plotted as slope, picoampere/milligram/deciliter (pA/mg/dL) versus age of cartridge (hours), over a three week use period after 5-month room temperature storage. Each cartridge includes an outer diffusion membrane of formula F20 (see Table 2).

Sensors (N=12) with outer membrane formulation, F20, demonstrated a creatinine sensor sensitivity remaining consistent over multiple batches over a 3-week use life after a 5-month room temperature storage. All sensors showed stable creatinine slopes (FIG. 1A) and stable creatine slopes (FIG. 1B), and a high Crea/Cr ratio as listed in Table 3. The data in Table 3 also demonstrates that the preferred Crea/Cr signal ratios were stable over a 5-month shelf life.

TABLE 3

Crea Sensor Slope Summary over shelf life using outer membrane formulation F20

| Use Life* (hour) | Crea Slope (pA/mg/dL) | Cr Slope (pA/mgAL) | Crea/Cr Slope Ratio |
|---|---|---|---|
| Shelf Life < 1 month | | | |
| 0-5 | 1731 | 530 | 3.3 |
| 20-30 | 1563 | 523 | 3.0 |
| 500 | 1038 | 384 | 2.7 |
| Shelf Life = 5 months | | | |
| 0-5 | 1339 | 372 | 3.6 |
| 20-30 | 1122 | 350 | 3.2 |
| 500 | 705 | 240 | 2.9 |

*The Use Life of a mutti-assay Crea/Cr cartridge with an outer membrane formulation as described herein is 450 samples or 500 hours.

Figure 2:
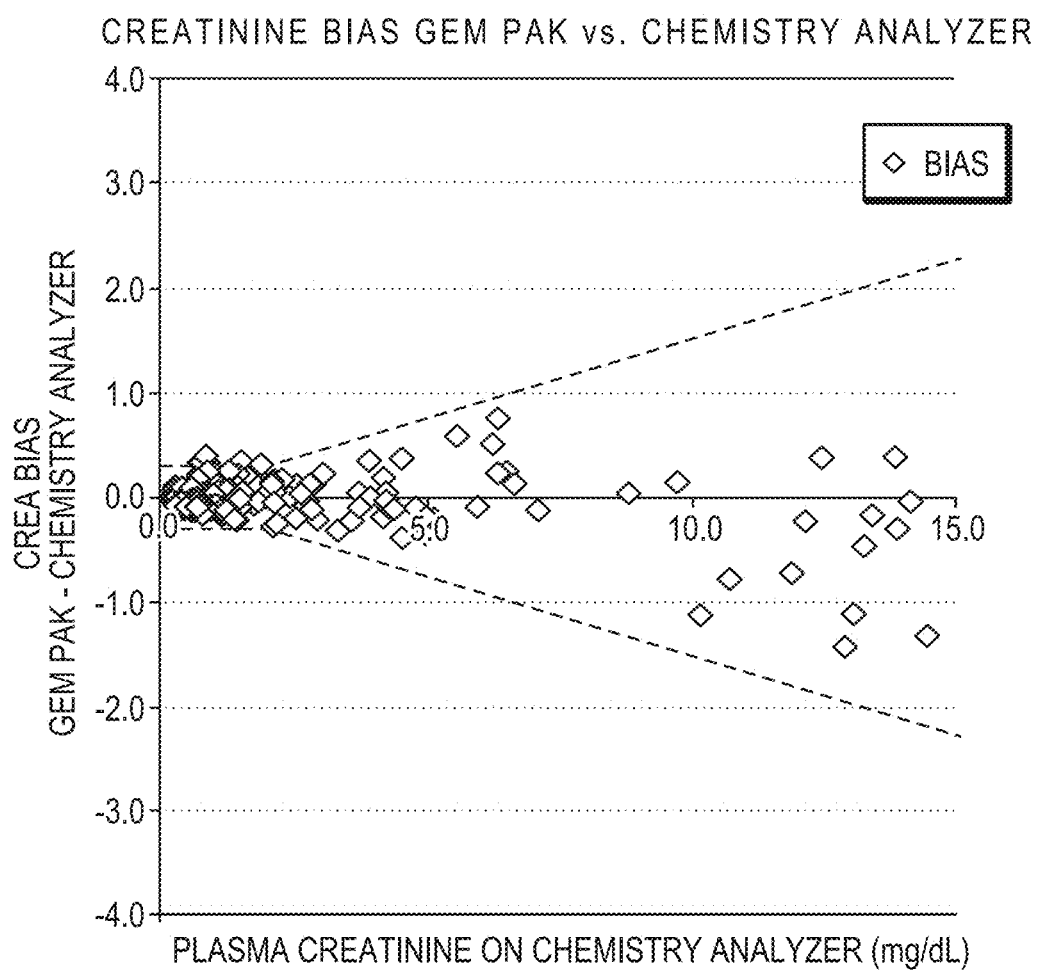
FIG. 2 is scatter plot depicting the bias of creatinine measured by whole blood creatinine biosensor vs. plasma creatinine on a chemistry analyzer (e.g., Roche Cobas). Each biosensor includes an outer diffusion membrane of formula F20 (see Table 2).

Example 3: Outer Membrane Formulation, F20, Biocompatibility and Sensor Baseline Recovery Whole blood creatinine in clinical samples was measured by creatinine sensors with outer membrane formulation, F20, and compared to plasma creatinine measured by chemistry analyzer, Roche Cobas. The sample biases were well within clinical requirements (dashed lines) (FIG. 2).

The results demonstrated the biocompatibility of outer membrane formulation, F20, when continuously exposed to clinical whole blood samples and exhibited stable performance compared to plasma results from a clinical laboratory analyzer. F20 also exhibited fast baseline recovery of a creatinine sensor during blood sample measurement. Creatinine accuracy was maintained throughout the measured sample range of 0.2-15 mg/dL, indicating that the impact from sample carryover was minimal.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodi-

I claim:

1. A biosensor comprising:
   an electrode;
   an enzyme layer on the electrode; and
   a diffusion membrane on the enzyme layer, the diffusion membrane comprising at least two different types of polyurethane materials, the at least two different types of polyurethane materials comprising (i) 50% to 55% w/w of 20% water uptake polyurethane and (ii) 45% to 50% w/w of 60% water uptake polyurethane;
   wherein the diffusion membrane has a creatinine to creatine diffusion ratio of at least 2.0.

2. The biosensor of claim 1, wherein the at least two different types of polyurethane materials comprise (i) 55% w/w of 20% water uptake polyurethane and (ii) 45% w/w of 60% water uptake polyurethane.

3. The biosensor of claim 1, wherein the at least two different types of polyurethane materials comprise at least three different types of polyurethane materials.

4. The biosensor of claim 3, wherein the at least three different types of polyurethane materials comprise 50% water uptake polyurethane.

5. The biosensor of claim 1, wherein the at least two different types of polyurethane materials comprise at least four different types of polyurethane materials.

6. The biosensor of claim 1, wherein the at least two different types of polyurethane materials comprise 45% w/w of 60% water uptake polyurethane.

7. The biosensor of claim 1, wherein the enzyme layer comprises at least one of creatininase, creatinase, or sarcosine oxidase.

8. The biosensor of claim 1, wherein the creatinine to creatine diffusion ratio is at least 3.0.

9. The biosensor of claim 1, wherein the creatinine to creatine diffusion ratio is stable over a 5-month shelf life at ambient storage.

10. The biosensor of claim 1, wherein the electrode comprises metal.

11. The biosensor of claim 10, wherein the metal comprises at least one of platinum, gold, palladium, or alloys comprised of platinum, gold, or palladium.

12. The biosensor of claim 1, wherein the electrode comprises carbon, graphite, or carbon nanotubes.

13. The biosensor of claim 1, wherein the enzyme layer comprises creatininase, creatinase, and sarcosine oxidase.

14. The biosensor of claim 13, wherein the creatinine to creatine diffusion ratio is at least 3.0.

15. The biosensor of claim 1, wherein the biosensor is configured to measure creatine and/or creatinine in a body fluid sample.

16. The biosensor of claim 15, wherein the body fluid sample comprises blood, plasma, or serum.

17. The biosensor of claim 1, wherein the creatinine to creatine diffusion ratio is stable over a 5-month shelf life at ambient storage.

18. The biosensor of claim 1, wherein the electrode comprises metal or carbon.

19. The biosensor of claim 18, wherein the metal comprises at least one of platinum, gold, palladium, or alloys comprised of platinum, gold, or palladium.

20. The biosensor of claim 19, wherein the carbon comprises graphite or carbon nanotubes.

21. The biosensor of claim 18, wherein the enzyme layer comprises two or more of creatininase, creatinase, or sarcosine oxidase.

22. The biosensor of claim 21, wherein the biosensor is configured to measure creatine and/or creatinine in a body fluid sample.

23. The biosensor of claim 22, wherein the body fluid sample comprises blood, plasma, or serum.

24. A disposable cartridge housing the biosensor of claim 1.

25. A method of making the diffusion membrane of the biosensor of claim 1, comprising:
   a) dissolving at least two different polyurethane resins in an organic solvent or mixture of solvents to create a polyurethane mixture;
   b) casting a layer of the polyurethane mixture onto a support material;
   c) allowing the solvent or mixture of solvents to evaporate; and
   d) repeating b) and c) 1-3 times.

26. The method of claim 25, wherein the different polyurethane resins have different water uptake percentages.

27. The method of claim 25, wherein the organic solvent comprises at least one of methylene chloride, dimethylformamide, dimethylacetamide, tetrahydrofuran, cyclohexanone, isopropanol, or a mixture of two or more of: methylene chloride, dimethylformamide, dimethylacetamide, tetrahydrofuran, cyclohexanone, or isopropanol.

28. The method of claim 25, wherein the support material comprises the electrode and the enzyme layer.

29. The method of claim 25, wherein b) and c) are repeated two times.

* * * * *